United States Patent [19]

Allison et al.

[11] Patent Number: 4,933,179

[45] Date of Patent: * Jun. 12, 1990

[54] FELINE LEUKEMIA VIRUS ANTIGEN VACCINES

[75] Inventors: Anthony C. Allison, Belmont; Noelene E. Byars, Sunnyvale, both of Calif.

[73] Assignee: Syntex (U.S.A.) Inc., Palo Alto, Calif.

[*] Notice: The portion of the term of this patent subsequent to Aug. 19, 2003 has been disclaimed.

[21] Appl. No.: 703,837

[22] Filed: Feb. 21, 1985

Related U.S. Application Data

[63] Continuation-in-part of Ser. No. 525,190, Aug. 22, 1983, Pat. No. 4,606,918.

[51] Int. Cl.$^5$ .......................................... A61K 39/225
[52] U.S. Cl. ........................ 424/89; 424/88; 424/93; 514/2; 514/8; 514/21; 514/723; 514/908; 514/975; 514/141; 530/322; 530/350; 530/395; 530/806; 435/235; 435/236; 435/237; 435/238; 435/239; 435/948; 252/21; 252/174; 252/351; 252/352
[58] Field of Search ................. 424/89, 88, 93; 514/2, 514/8, 723, 908, 975, 941; 530/322, 806, 350, 395; 252/174.21, 351, 352; 435/235–239, 948

[56] References Cited

U.S. PATENT DOCUMENTS

| | | | |
|---|---|---|---|
| 2,674,619 | 4/1954 | Lundsted | 252/174.21 |
| 3,867,521 | 0/0000 | Miskel et al. | 424/78 |
| 3,869,546 | 0/0000 | Lund | 424/88 |
| 3,869,549 | 0/0000 | Geller | 514/2 |
| 3,966,907 | 6/1976 | Jarrett | 424/89 |
| 4,034,081 | 7/1977 | Jarrett | 424/89 |
| 4,082,735 | 0/0000 | Jones et al. | 514/2 |
| 4,082,736 | 0/0000 | Jones et al. | 514/2 |
| 4,086,134 | 4/1978 | Jarett | 424/89 |
| 4,101,536 | 0/0000 | Yamamura et al. | 514/2 |
| 4,117,112 | 9/1978 | Jarrett | 424/89 |
| 4,148,869 | 0/0000 | Deaton | 424/1.1 |
| 4,158,052 | 0/0000 | Audibert et al. | 424/45 |
| 4,185,089 | 0/0000 | Derrein et al. | 424/88 |
| 4,220,637 | 0/0000 | Audibert et al. | 424/88 |
| 4,264,587 | 4/1981 | Pedersen | 424/89 |
| 4,314,998 | 0/0000 | Yamamura et al. | 514/2 |
| 4,323,559 | 0/0000 | Audibert et al. | 514/2 |
| 4,323,560 | 0/0000 | Bashang et al. | 514/2 |
| 4,332,793 | 6/1982 | Olson | 424/89 |
| 4,369,178 | 0/0000 | Yamamura et al. | 514/2 |
| 4,382,080 | 5/1983 | Shiba et al. | 514/2 |
| 4,384,974 | 0/0000 | Guthauser et al. | 424/59 |
| 4,397,870 | 0/0000 | Sloviter | 514/672 |
| 4,406,885 | 9/1983 | Pinter | 424/88 |
| 4,406,889 | 0/0000 | Hartmann et al. | 514/2 |
| 4,409,209 | 0/0000 | Baschang et al. | 514/2 |
| 4,423,038 | 0/0000 | Baschang et al. | 514/2 |
| 4,427,659 | 0/0000 | Le Francier et al. | 514/2 |
| 4,434,157 | 2/1984 | Olsen | 424/89 |
| 4,461,761 | 0/0000 | Le Francier et al. | 514/2 |
| 4,606,918 | 8/1986 | Allison | 424/88 |
| 4,663,436 | 5/1987 | Elder | 424/88 |

FOREIGN PATENT DOCUMENTS

3308458-A  9/1984  Fed. Rep. of Germany.

OTHER PUBLICATIONS

Gilbert, J. H. et al, Virus Research 7(1): 49–67 (1987) cited in Chem. Abst. CA 106(19):150687a.
Pedersen, N. C. et al, Veter. Immunol. Immunopathol, 11(2): 123–148 (1986) cited in Chem. Abst. CA104(25):223024c.
Luciu, P. et al, Basic Life Science, 37:207–215 (1986) cited in Chem. Abst. CA105(13):113218g.
Hunter, et al., *J. Immunol.*, 127, 1244 (1981).
Hunter, et al., *Rev. Cancer Res.*, 3, 279–286 (1980).
Snippe, et al., *Int. Archs. Allergy Appl. Immun.*, 65, 390–398 (1981).

*Primary Examiner*—Margaret Moskowitz
*Assistant Examiner*—Jeff Kushan
*Attorney, Agent, or Firm*—Carol J. Roth; Derek P. Freyberg; Tom M. Moran

[57] ABSTRACT

A vaccine for immunizing animals against Feline Leukemia Virus (FeLV) infections contains an FeLV antigen emulsified with a polyoxypropylene-polyoxyethylene block polymer, a glycol ether-based surfactant, an immunopotentiating amount of an immunostimulating glycopeptide, and, optionally, a metabolizable nontoxic oil.

26 Claims, No Drawings

FELINE LEUKEMIA VIRUS ANTIGEN VACCINES

This Patent is a Continuation In Part of U.S. Pat. Appn. Ser. No. 525,190 filed Aug. 22, 1983 now U.S. Pat. No. 4,686,918.

BACKGROUND OF THE INVENTION

This invention relates to Feline Leukemia Virus (FeLV) vaccines. More particularly, this invention relates to a method for enhancing the immunogenicity of an FeLV antigen by emulsifying it with a polyoxypropylene-polyoxyethylene block polymer, a glycol ether-based surfactant, an optional metabolizable non-toxic oil, and an immunopotentiating amount of an immunostimulating glycopeptide.

This invention also relates to a method for protecting cats from Feline Leukemia Virus (FeLV) infections by administering the vaccine of the invention.

RELATED DISCLOSURES

Feline Leukemia virus (FeLV) is an oncorna virus, a RNA virus capable of causing lymphoid malignancies in cats. It may also cause anemia, reproductive difficulties, and myeloproliferative disorders in infected animals. It occurs in three antigenically similar types, referred to as A, B, and C (see, e.g., Sarma et al., *Virology*, 54, 160-169 (1973)). Strain KT-FeLV, a strain commonly used in FeLV vaccines, produces all three sera types. Strain R-FeLV produces only sera type A.

FeLV is believed to be transmitted horizontally through cat populations. After exposure, an animal will either develop immunity or will become chronically infected. In dense cat populations, nearly all exposed cats become infected, and one-third or more may become persistently infected.

Vaccines for FeLV may be evaluated in terms of the serum antibody titer to whole virus, or by challenge with active virus.

FeLV antigens known in the art are prepared from whole FL74 cells (a feline lymphoma strain persistently infected with virus strain KT-FeLV) with FeLV particles bound to the cell membrane (Jarrett, U.S. Pat. Nos. 4,117,112, 4,034,081, 3,996,907), from KT-FeLV particles inactivated with aqueous formaldehyde (Pederson, U.S. Pat. No. 4,264,587), or isolated viral capsid proteins (Olsen, U.S. Pat. No. 4,434,157; Pinter, U.S. Pat. No. 4,406,885).

Freund's discovery that the immunogenicity of antigens could be potentiated by emulsifying an aqueous antigen solution with mineral oil alone or with mineral oil and *M. tuberculosis*, formed the basis of the concept of using a secondary material to increase a subject's humoral and cell-mediated immune responses to an antigen. An essential component of Freund's complete and incomplete adjuvant is mineral oil. This component plays a central role in effecting an increased humoral response to the antigen. However, mineral oil is believed to cause granulomas and other undesirable side effects. The mycobacteria in complete Freund's adjuvant are essential for significantly enhanced cellular immunity.

Though little attention was initially paid to the role the surfactant may play in Freund's incomplete or complete adjuvant, subsequent research has indicated that in several instances a surfactant may demonstrate adjuvant properties in and of itself. A number of naturally occurring surface active agents such as the lipid A portion of endotoxin of gram negative bacteria and trehalose dimycolate of mycobacteria are among the most potent adjuvants of these naturally occurring surfactants. A constituent of mammalian cells, the phospholipid lysolecithin also has been shown to have adjuvant activity. (B. Arnold et al, *Eur. J. Immunol.*, 9: 363-366 (1979).)

In addition, several synthetic surfactants, for example, dimethyldioctadecyl ammonium bromide (DDA) and certain polyoxypropylene-polyoxyethylene block polymers have been reported as having adjuvant activity. (See H. Snippe et al, *Int. Archs. Allergy Appl. Immun.*, 65: 390-398 (1981). In addition, R. Hunter et al, have reported in the *Journal of Immunology*, 127: 1244-1250 (1981) that polyoxypropylene-polyoxyethylene block polymers, when used as the surfactant component of an oil-in water based adjuvant formulation, increase antibody formation to BSA in mice.

While these natural and synthetic surfactants demonstrate a certain degree of adjuvanticity, results so far published demonstrate that, except for DDA, none of the surfactants when used alone matches the immunopotentiating activity found when using complete or incomplete Freund's adjuvant. However, it is not possible to use either Freund's incomplete or complete adjuvant for general vaccination purposes because both mineral oil and mycobacteria have deleterious side effects when injected subcutaneously. As a result, Freund's adjuvants have not been authorized for domestic animal or human use by governmental regulatory agencies.

However, there is a substantial need for some means of potentiating the immunogenicity of antigens. This is particularly true because virus subunit and other protein antigens which are now being prepared by recombinant DNA technology have been shown to be poor immunogens when used alone. Moreover, naturally occurring or synthetic peptide fragments from larger proteins known to be antigenic are being administered rather than whole proteins or a mixture of materials containing the whole proteins.

To elicit useful immune responses, antigenic proteins and haptens must be administered with some type of adjuvant. Neither Freund's complete or incomplete adjuvant can be used, as noted above. Glycopeptides derived from the mycobacteria of Freund's adjuvant should be able to provide the needed immunopotentiation (Ellouz et al. *Biochem. & Biophys. Res. Comm.*, Vol 59, 4, 1317 (1974)), but these materials are most effective when presented to the subject as an emulsion. Since mineral oil may not be used due to its toxicity, an alternative emulsion-forming material is needed for administering antigens.

It has now been found that when immunopotentiating glycopeptides and an antigen are emulsified with a nontoxic polyoxypropylene-polyoxyethylene block polymers and a multiphase-stabilizing amount of a glycol ether-based non-toxic surfactant, the immunogenicity of the antigen is increased in the same manner and to approximately the same degree as when mineral oil is used. It has been found that the block polymer is critical to achieving an immune response but that a maximal response is most effectively achieved only when the multiphase system is stabilized by some detergent such as a non-ionic glycol ether-based surfactant. The presence of a metabolizable oil may enhance the effectiveness of these formulations as well. Because the polyoxypropylene-polyoxyethylene block polymers and glycol ether surfactants are non-toxic, this adjuvant formulation may be safely used as a vehicle for enhancing the immunogenicity of antigens administered to birds and mammals, particularly to cats.

SUMMARY OF THE INVENTION

One aspect of the invention is a vaccine for immunizing birds and mammals against FeLV, which comprises an FeLV antigen emulsified with a polyoxypropylene-polyoxyethylene block polymer, a glycol ether-based surfactant, a metabolizable non-toxic oil, and an immunopotentiating amount of an immunostimulating glycopeptide.

Another aspect of the invention is a method for enhancing the immunogenicity of an FeLV antigen which method comprises emulsifying an FeLV antigen with an adjuvant vehicle comprising an immunopotentiating amount of a glycopeptide, a multi-phase forming amount of a non-toxic polyoxypropylene-polyoxyethylene block copolymer, a multiphase-stabilizing amount of a glycol ether-based surfactant, optionally a metabolizable oil, and buffered aqueous solution in a quantity sufficient to make volume.

Another aspect of the invention is the method of immunizing a bird or mammal, especially a cat, against FeLV by administering to said bird or mammal an immunogenic amount of a vaccine of the invention.

DETAILED DESCRIPTION

As set out above, the uniqueness of this invention lies in the use of a polyoxypropylene-polyoxyethylene block polymer in combination with a second surfactant such as glycol ether-based surfactant as an adjuvant vehicle which, when formed into an emulsion or suspension with an immunopotentiating glycopeptide and an FeLV antigen, potentiates the immunogenicity of the FeLV antigen. This composition is further unique in that it can be safely administered to birds and mammals. Thus it is possible to prepare injectable vaccines wherein the antigen will elicit humoral and cell mediated immune responses comparable to those that can be obtained if the antigen is administered in Freund's incomplete or complete adjuvant. A vaccine with such properties will serve to reduce the number of times an antigen must be administered in order to develop a protective response in the subject. In addition, the amount of antigen required to elicit a protective response can be reduced.

The polyoxypropylene-polyoxyethylene (POP-POE) block polymers of this invention are a widely available material commercially known by the trademark Pluronic ® polyols. These compounds are made by the sequential addition of propylene oxide and then ethylene oxide to a low molecular weight, reactive hydroxy compound, usually propylene glycol. The characteristics of these polyols are determined by the molecular weight of the polyoxyethylene glycol midsection and of the ratio of polyoxypropylene to polyoxyethylene in the polymer. Polyoxypropylene glycols with a molecular weight of approximately 900 or more are water insoluble and impart hydrophobic characteristics to the polyol. The polyethylene glycol component, which usually constitutes from 10% to 90% of the total weight, imparts water-soluble properties to the polymer, thus resulting in a compound having surface active properties.

POP-POE block polymers may be represented empirically by the formula:

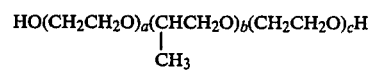

wherein a and c are statistically equal. These compounds can be prepared by the methods set out in U.S. Pat. No. 2,674,619 issued to Lunsted. The most common means of making the compound is to react a bifunctional initiator, e.g., propylene glycol, with propylene oxide in the presence of a catalytic amount of anhydrous sodium hydroxide and allowing the reaction to proceed until the desired molecular weight is obtained. A predetermined amount of ethylene oxide is then added to the same reaction pot to make the block polymer.

These block polymer polyols range in molecular weight from approximately 1,000 up to 16,000. The polymers of particular interest to this invention are those having an average molecular weight between about 2,000 and 15,500. Such materials are commercially available from several sources, for example, BASF-Wyandotte Corp., Parsippany NJ. and E. I. Du pont.

POP-POE polyols available from BASF-Wyandotte under the name Pluronic ® are identified by a letter prefix followed by a two or a three digit number. The letter prefixes are L, P and F and refer to the physical form of each polymer, L-liquid, P-paste, or F-flakeable solid. The two and three digit numbers are used to designate the average molecular weight of the polyoxypropylene hydrophobic midsection in comparison with the percent polyoxyethylene in the total molecule. For example, the first two digits of "L-101" indicate that the polyoxypropylene midsection has an average molecular weight of 3,250 while the third digit indicates that the polymer is 10% polyoxyethylene by weight (w/w). In "F-108," the "10" designates a polyoxypropylene midsection with an average molecular weight of 3,250 and the "8" designates that polyoxyethylene comprises 80% (w/w) of the total molecule.

The block polymers of greatest interest to this invention are those which are liquid over a temperature range between about 15°–40° C. In addition, polymer mixtures of liquid and paste, liquid, paste and flakeable solid or liquid and flakeable solid mixtures which are liquid within the specified temperature range have utility in this invention.

Preferred block polymers are those having a POP midsection ranging in molecular weight between about 2250 and 4300 and POE in an amount between about 1 and 30% (w/w). More preferred are those polymers wherein POP has a molecular weight falling between 3250 and 4000 and the POE component comprises 10–20%. The Pluronic ® polyols L-101, L-121 and L-122 fall within this definition. Most preferred are the polymers wherein POE comprises about 10% (w/w) of the polymer and the POP midsection has a molecular weight of about 4000 or about 3250, e.g., Pluronic ® polyols L-121 and L-101 respectively.

A multi-phase forming amount of polymer is that quantity which will form micelles, or more broadly, a system characterized as an emulsion or suspension. For the purposes of this invention, that amount is between 0.2% and 49% by volume. A more preferred amount is between 0.2% and 20% (v/v), though no more than 5% is even more preferred and 2.5% is most preferred.

The efficacy of these compositions can best be realized by employing a non-toxic, non-ionic detergent to stabilize the emulsion or suspension formed. If the block polymer alone is used, the antigen will show some increased immunogenicity but the effect will be smaller in comparison with the effect observed when the non-ionic detergent is present. This non-ionic detergent may also be characterized as an emulsifying or suspending agent in that it is present for achieving those two purposes and is present in a minor amount in comparison to the block polymer.

A substantial number of emulsifying and suspending agents are generally used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and polyfunctional compounds. Long chain fatty acid-derived compounds form a third substantial group of emulsifying and suspending agents which could be used in this invention. Though any of the foregoing surfactants are useful so long as they are non-toxic, the glycol ether derived compounds are the preferred emulsifying agents in this invention.

The simplest member of the family of compounds based on the glycol ethers is ethylene oxide. The internal or cyclic ethers of the simplest glycol, ethylene glycol, mono- and diethers of ethylene glycol are also well-known. One important group of glycol ethers is the polyethylene glycols. The compounds of most interest herein are PEG b 200, 300, 400, 600 and 900.

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty acid substituted moiety may be further reacted with ethylene oxide to give a second group of surfactants.

The fatty acid substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common name for these surfactants are for example sorbitan monolaurate, sorbitan monopalmitate, sorbitan monostearate, sorbitan monooleate, sorbitan sesquioleate, sorbitan trioleate. These surfactants are commercially available under the name SPAN or ARLACEL, usually with a letter or number designation which distinguishes between the various mono-, di- and triester substituted sorbitans.

SPAN and ARLACEL surfactants are hydrophilic and are generally soluble or dispersible in oil and tend to form water-in-oil emulsions. They are also soluble in most organic solvents. In water they are generally insoluble but dispersible. Generally these surfactants will have a hydrophilic-lipophilic balance (HLB) number between about 1.8 to 8.6. Such surfactants can be readily made by means known in the art or are commercially available from, for example, ICI, America's Inc., Wilmington, Del. under the registered mark Atlas ®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN ®, are useful for preparing oil-in-water emulsions and dispersions, or for the solubilization of oils and making anhydrous ointments water-soluble or washable. The TWEEN surfactants may be combined with a relates sorbitan monoester or triester surfactants to promote emulsion stability. TWEEN surfactants generally have a HLB value falling between 9.6 to 16.7. TWEEN surfactants are commercially available from a number of manufacturers, for example ICI, America's Inc., Wilmington, Del. under the registered mark Atlas ® surfactants.

A third group of non-ionic surfactants which could be used alone or in conjunction with SPAN, ARLACEL and TWEEN surfactants are the polyoxyethylene fatty acids made by the reaction of ethylene oxide with a long-chain fatty acid. The most commonly available surfactant of this type is sold under the name MYRJ ® and is a polyoxyethylene derivative of stearic acid. MYRJ ® surfactants are hydrophilic and soluble or dispersible in water like TWEEN ® surfactants. The MRYJ ® surfactants may be blended with TWEEN ® surfactants or with TWEEN ®/SPAN ® or ARLACEL ® mixtures for use in forming emulsions. MYRJ ® surfactants can be made by methods known in the art or are available commercially from ICI America's Inc.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ ®. BRIJ ® surfactants may be hydrophilic or lipophilic depending on the side of the polyoxyethylene moiety in the surfactant. While the preparation of these compounds is available from the art, they are also readily available from such commercial sources as ICI America's Inc.

Other non-ionic surfactants which can potentially be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohol or ether derivatives of long-chain fatty acids of 12-21 carbon atoms.

As the adjuvant and the vaccine formulations of this invention are intended to be multi-phase systems, it is preferable to choose an emulsion-forming non-ionic surfactant which has an HLB value in the range of about 7 to 16. This value may be obtained through the use of a single non-ionic surfactant such as a TWEEN ® surfactant or may be achieved by the use of a blend of surfactants such as with a sorbitan mono-, or di- or triester with an compatible polyoxyethylene soribitan mono- or triester based surfactant; a sorbitan ester-polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single non-ionic surfactant, most particularly a TWEEN ® surfactant, as the emulsion stabilizing non-ionic surfactant in the practice of this invention. The surfactant named TWEEN ®80, otherwise known as polysorbate 80 for polyoxyethylene 20 sorbitan monooleate, is the most preferred of the foregoing surfactants.

Multiphase stabilization can usually be effected by having the surfactant present in an amount of 0.05% to 2.5% by weight (w/w). An amount of 0.2% to 1% is preferred.

The immune response stimulating glycopeptides of this invention are a group of compounds related to and derived from N-acetylmuramyl-L-alanyl-D-isoglutamine, which was determined by Ellouz et al, *Biochem. & Biophys. Res. Comm.*, Vol 59, 4, 1317 (1974) to be the smallest effective unit possessing immunological adjuvant activity in *M. tuberculosis*, the mycobacterial component of Freund's complete adjuvant. A number of dipeptide- and polypeptide-substituted muramic acid derivatives were subsequently developed and found to have immunostimulating activity.

Though these glycopeptides are a diverse group of compounds, they can be generally represented by the formula

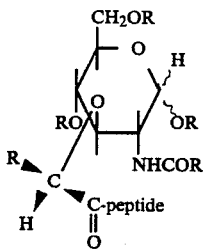

wherein the pyran ring oxygens are substituted by hydrogen, alkyl, or acyl or the like, or may be replaced by nitrogen-based substituents, particularly the 6-position oxygen; the 2-amino group is an acyl group or some other amide, the lactyl side chain is modified, e.g. is ethyl or another two-position alkyl moiety; and the peptide function is a dipeptide or polypeptide. Furanosyl analogs of the pyranosyl compounds also have immunopotentiating activity and are useful in this invention.

Among the glycopeptides of this invention are those disaccharides and tetrasaccharides linked by meso-α-ε-diaminopimelic acid such as described in U.S. Pat. Nos. 4,235,771 and 4,186,194.

Immune response stimulating glycopeptides which may be used in the practice of this invention are disclosed in U.S. Pat. Nos. 4,094,971; 4,101,536; 4,153,684; 4,235,771; 4,323,559; 4,327,085; 4,185,089; 4,082,736; 4,369,178, 4,314,998 and 4,082,735; and 4,186,194. The glycopeptides disclosed in these patents are incorporated herein by reference and made a part hereof as if set out in full herein. The compounds of Japanese patent applications J5 4079-227, J5 4079-228, and J5 41206-696 would also be useful in the practice of this invention.

Methods for preparing these compounds are disclosed and well-known in the art. Preparative process exemplification can be found in U.S. Pat. Nos. 4,082,736 and 4,082,735. Additional, similar preparative processes may be found in the U.S. patents referenced in the preceding paragraph.

Preferred glycopeptides are those having the Formula I

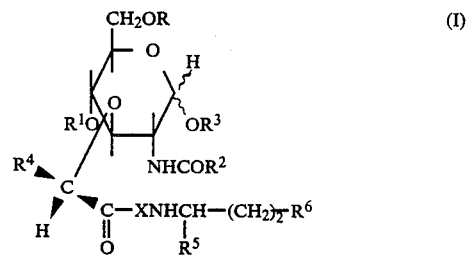

wherein
R and $R^1$ are the same or different and are hydrogen or an acyl radical containing from 1 to 22 carbon atoms;

$R^2$ is an unsubstituted or substituted alkyl radical containing from 1 to 22 carbon atoms, or an unsubstituted or substituted aryl radical containing from 6 to 10 carbon atoms;

$R^3$ is hydrogen, alkyl of 1 to 22 carbons, or aryl of 7 to 10 carbon atoms;

$R^4$ is hydrogen or alkyl;

X is alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparaginyl, prolyl, hydroxyprolyl, seryl, or glycyl;

$R^5$ is an optionally esterified or amidated carboxyl group; and $R^6$ is an optionally esterified or amidated carboxyl group.

Alkyl is a straight or branched radical comprised of 1 to 7 carbon atoms unless otherwise specified, exemplified by methyl, ethyl, propyl, butyl, pentyl, hexyl or heptyl or an isomer. Lower alkyl is a radical of 1 to 4 carbon atoms.

An optionally substituted benzyl radical is that benzyl radical which is optionally mono-substituted, di-substituted, or poly-substituted in the aromatic nucleus, for example, by lower alkyl, free, etherified or esterified hydroxyl or mercapto groups, for example, lower alkoxy or lower alkylene dioxy groups, as well as lower alkyl mercapto or trifluoromethyl groups and/or halogen atoms.

An optionally esterified or amidated carboxyl group is the carboxyl group itself or a carboxyl group esterified with a lower alkanol, such as methanol, ethanol, propanol, butanol, or the carbamoyl group, which, on the nitrogen atom, is unsubstituted or mono-substituted or di-substituted by alkyl, especially lower alkyl, aryl, particularly phenyl, or arylalkyl, particularly benzyl. The carbamoyl group may also be substituted with an alkylidene radical such as butylidene or pentylidene radical. In addition, the carbamoyl group $R_5$ may also be substituted with a carbamoylmethyl group on the nitrogen atom.

Particularly preferred compounds are those of Formula 1 wherein R and $R^1$ are the same or different and are hydrogen or an acyl radical containing from 1 to 22 carbon atoms; $R^2$ is methyl; $R^3$ is hydrogen; and X is L-seryl, L-alanyl, L-valyl, L-leucyl, L-isoleucyl, L-α-aminobutyryl, L-seryl, L-threonyl, L-methionyl, L-cysteinyl, L-phenylalanyl, L-tyrosyl, L-tryptophenyl, L-lysyl, L-ornithyl, L-arginyl, L-histidyl, L-glutamyl, L-glutamanyl, L-aspartyl, L-asparaginyl, L-prolyl, or L-hydroxyprolyl.

A more preferred group of glycopeptides are the compounds of Formula 1 wherein R and $R^1$ are hydrogen or acyl of 1 to 22 carbon atoms, $R^2$ is methyl, $R^3$ is hydrogen and $R^4$ is methyl or butyl, and X is L-valyl, L-seryl, L-alanyl, L-threonyl or L-α-aminobutyryl.

Most particularly preferred are the following compounds:

N-acetylmuramyl-L-α-aminobutyrul-D-isoglutamine;
6-O-stearoyl-N-acetylmuramyl-L-α-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-isoglutamine;
N-acetyl-desmethylmuramyl-L-alanyl-D-isoglutamine;
N-acetylmuramyl-L-alanyl-D-glutamine n-butyl ester;
N-acetylmuramyl-L-seryl-D-isoglutamine;
N-acetyl(butylmuramyl)-L-α-aminobutyryl-D-isoglutamine; and
N-acetyl(butylmuramyl)-L-alanyl-D-isoglutamine.

An effective amount of immunostimulating glycopeptide is that amount which effects an increase in titer level when administered in conjunction with an antigen over that titer level observed when the glycopeptide has not been co-administered. As can be appreciated, each glycopeptide may have an effective dose range that may differ from the other glycopeptides. Therefore, a single dose range cannot be prescribed which will have a precise fit for each possible glycopeptide within the scope of this invention. However, as a general rule, the glycopeptide will preferably be present in the vaccine in an amount of between 0.001 and 5% (w/v). A more preferred amount is 0.01 to 3% (w/v).

Another component of these formulations, which may be present at the option of the formulator, is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the animal or bird to which the adjuvant will be administered and which is not toxic to the organism. Mineral oil and similar toxic petroleum distillate oils are expressly excluded from this invention.

The optional oil component of this invention may be any long chain alkane, alkene or alkyne, or an acid or alcohol derivative thereof either as the free acid, its salt or an ester such as a mono-, di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will have 6–30 carbon atoms. The moiety may have a straight or branched chain structure. It may be fully saturated or have one or more double or triple bonds. Where mono or poly ester- or ether-based oils are employed, the limitation of 6–30 carbons applies to the individual fatty acid or fatty alcohol moieties, not the total carbon count.

Any metabolizable oil, particularly from an animal, fish or vegetable source, may be used herein. It is essential that the oil be metabolized by the animal or bird to which it is administered, otherwise the oil component may cause abscesses, granulomas or even carcinomas, or may make the meat of vaccinated birds and animals unacceptable for human consumption due to the deleterious effect the unmetabolized oil may have on the consumer.

Sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is readily available but the oil of other cereal grains such as wheat, oats, rye, rice, triticale and the like may also be used.

The technology for obtaining vegetable oils is well developed and well known. The compositions of these and other similar oils may be found in, for example, the Merck Index, and source materials on foods, nutrition and food technology.

The 6–10 carbon fatty acid esters of glycerol and 1,2-propanediol, while not occurring naturally in seed oils, may be prepared by hydrolysis, separation and esterification of the appropriate materials starting from the nut and seed oils. These products are commercially available under the name "Neobee" from PVO International, Inc., Chemical Specialities Division, 416 Division Street, Boongon, N.J. and others. Reference is made to U.S. patent application Ser. No. 341,403, filed Jan. 21, 1982 for methods for making these latter materials.

Oils from any animal source, including birds, may be employed in the adjuvants and vaccines of this invention. Animal oils and fats are usually solids at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. Shark liver oil contains a branched, unsaturated oil known as squalene, 2,6,10,15,19,23-hexamethyl-2,6,10,14,18,22-tetracosahexaene which is particularly preferred herein. Squalane, the saturated analog of squalene is also a particularly preferred oil. Fish oils, including squalene and squalane, are readily available from commercial sources or may be obtained by methods known in the art.

The oil component of these adjuvants and vaccine formulations will be present in an amount from 1% to 30% by weight but preferably in an amount of 1% to 10% w/v. It is most preferred to use a 5% w/v concentration of oil.

The aqueous portion of these adjuvant compositions is buffered saline. Because these compositions are intended for parenteral administration, it is preferable to make up these solutions so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components, such as the glycopeptides.

Any physiologically acceptable buffer may be used herein, but phosphate buffers are preferred. Other acceptable buffers such as acetate, tris, bicarbonate, carbonate, or the like may be used as substitutes for phosphate buffers.

The pH of the aqueous component will preferably be between 6.0–8.0 though it is preferable to adjust the pH of the system to 6.8 where that pH does not significantly reduce the stability of other composition components and is not otherwise physiologically unsuitable.

The quantity of buffered saline employed in these compositions will be that amount necessary to bring the value of the composition to unity. That is, a quantity of buffered saline sufficient to make 100% will be mixed with the other components listed above in order to bring the composition to volume.

The word antigen refers to any substance, including a protein or protein-polysaccharide, protein-lipopolysacchride, polysaccharide, lipopolysaccharide, viral subunit, whole virus or whole bacteria which, when foreign to the blood stream of a bird or animal, on gaining access to the tissue of such an animal stimulates the formation of specific antibodies and reacts specifically in vivo or in vitro with a homologous antibody. Moreover, it stimulates the proliferation of T-lymphocytes with receptors for the antigen, and can react with the lymphocytes to initiate the series of responses designated cell-mediated immunity.

A hapten is within the scope of this definition. A hapten is that portion of an antigenic molecule or antigenic complex that determines its immunological specificity. Commonly, a hapten is a peptide or polysaccharide in naturally occurring antigens. In artificial antigens it may be a low molecular weight substance such as an arsanilic acid derivative. A hapten will react specifically in vivo and in vitro with homologous antibodies or T-lymphocytes. Alternative descriptors are antigenic determinant, antigenic structural grouping and haptenic grouping.

The formulation of a vaccine of the invention will employ an effective amount of an FeLV antigen. That is, there will be included an amount of antigen which, in combination with the adjuvants, will cause the subject to produce a specific and sufficient immunological response so as to impart protection to the subject from the subsequent exposure to FeLV.

FeLV antigens may be produced, for example, by the methods described in U.S. Pat. Nos. 4,434,157, 4,406,885, 4,264,587, 4,117,112, 4,034,081, 3,996,907, incorporated herein by reference, or by culturing normal cat embryo (NCE) cells, infecting the cells with R-FeLV, harvesting the virus, and inactivating the virus with 0.3% aqueous formalin.

No single dose designation can be assigned which will provide specific guidance for each and every antigen which may be employed in this invention. The effective amount of antigen will be a function of its inherent activity and purity. It is contemplated that the adjuvant compositions of this invention may be used in conjunction with whole cell or virus vaccines as well as with purified antigens or protein subunit or peptide vaccines prepared by recombinant DNA techniques or synthesis.

Adjuvant preparations are readily made by well known art methods. For example, one can make a 2-fold concentrated solution of the antigen and glycopeptide in the buffered saline. A two-fold concentration of the block polymer, oil, and multiphase stabilizing surfactant is mixed with buffered saline; then the first and second solution are mixed.

A further understanding of the invention may be had from the following non-limiting examples.

PREPARATION 1

The Rickard Feline Leukemia Virus (R-FeLV) used in the vaccine was originally isolated from the tissue of a leukemic cat and adapted to grow in cell culture. The cell line used to propagate the virus is a persistently infected feline line, NCE-F161, obtained from Dr. Fernando de Noronha, Cornell University, Ithaca, N.Y. The cell line was received at passage 49. The infected cell line was deposited on Feb. 20, 1985 with the American Type Culture Collection, Rockville, Md., ATCC No. CRL-8727.

The growth and maintenance media used for seed and production cultures was Dulbecco's minimum essential medium (4500 mg glucose/liter) supplemented with 10 percent bovine calf serum, 10 mM HEPES buffer, penicillin (up to 30 units/ml), streptomycin (up to 30 $\mu$g/ml), and mycostatin (up to 10 units/ml). The cells were grown in roller bottles of 850 $cm^2$ or 2000 $cm^2$ surface area. Plastic or glass bottles were used for cell propagation. A cell suspension was added to the roller bottles at a rate of $3\times10^7$ cells in approximately 500 ml growth medium per 850 $cm^2$ roller bottle and $7\times10^7$ cells in approximately 1500 ml growth medium per 2000 $cm^2$ roller bottle.

Three to six days following the final cell planting, the cell-free virus fluids were harvested. At time of harvest, roller bottle cultures were refed with 500 ml of growth medium per roller bottle containing 700–1000 $\mu$g of microcarriers (available commercially from Pharmacia Fine Chemicals, New Jersey) per 850 $cm^2$ roller bottle and 1.7–2.4 mg of microcarriers per 2000 $cm^2$ roller bottle to increase the available surface area. Virus fluids were harvested at 3 to 5 day intervals for an additional 2 to 4 harvests.

Virus fluids were harvested using standard harvest techniques. Specifically, the virus fluids were aseptically transferred to harvest containers from which samples were taken for virus titration and purity evaluation. Virus produced by this method resulted in bulk virus titers of equal to or greater than $10^{4.5} TCID_{50}$/ml.

The virus was inactivated by addition of formalin to a final concentration of 0.3 percent. The formalin-treated fluids were maintained at approximately 20° C. for 24–72 hours under agitation and samples were removed to check for inactivation. Merthiolate was then added to a concentration of 1:10,000.

Inactivated virus fluids were concentrated prior to the preparation of the vaccine. Sterile sodium chloride solution (5M) was added to the virus fluids to give a final concentration of 0.5M sodium chloride. A sterile 40% polyethylene glycol 6000 (PEG 6000) stock solution was added to the virus fluids to give a final concentration of 5% PEG. While maintaining the temperature at approximately 4° C., the fluids were stirred for 1–4 hours, then allowed to stand an additional 12 to 18 hours. After precipitation, the fluids were processed by centrifugation. The resulting pellet was resuspended in phosphate buffered saline containing Merthiolate to give a concentration equivalent to 50 to 100 ml of bulk virus fluids per one ml of concentrate (milliliter equivalents).

EXAMPLE 1

A Pluronic ®-based vaccine was prepared as follows:

| Solution I | | |
|---|---|---|
| Sodium Chloride | 80.0 g | |
| Potassium Chloride (KCl) | 2.0 g | |
| Potassium Phosphate ($KH_2PO_4$) | 2.0 g | |
| Dibasic Sodium Phosphate ($Na_2HPO_4 \cdot 7H_2O$) | 21.6 g | |
| Tween 80 | 40.0 ml | |
| Distilled water q.s. | 10,000.0 ml | |
| Solution II | | |
| N-acetyl-D-muramyl-L-threonyl-D-isoglutamine | 0.6 g | |
| Solution I | 50.0 ml | |
| Complete adjuvant assembly | | |
| | Percent | |
| Solution I | 84.5 | 8450.0 ml |
| Solution II | 0.5 | 50.0 ml |
| Squalene | 10.0 | 1,000.0 ml |
| Pluronic ® L-121 | 5.0 | 500.0 ml |

The Pluronic ®-based vaccine was formulated by mixing one part virus concentrate with one part adjuvant.

EXAMPLE 2

Two doses of the vaccine were administered to test cats 5 weeks and 2 weeks prior to challenge with FeLV. The control group received no injections. The cats used were specific pathogen-free domestic, short-haired kittens, 11–12 weeks old, obtained from Liberty Laboratories, Liberty Corners, N.J.

FeLV grown in FC-9 cells was used as the challenge virus to infect the cats by the oronasal route. All cats received methylprednisolone acetate (10 mg/kg) following challenge.

Weekly blood samples were obtained from all cats beginning 2 weeks post-challenge and continuing for 11 weeks post-challenge. Blood samples were tested for viral antigens by indirect fluorescent antibody techniques and for p27 antigens by enzyme-linked immunosorbent assay (ELISA) (see Engvall and Perlman, *J. Immunol,* 109: 129–35, 1972).

What is claimed is:

1. A vaccine for immunizing an animal against feline leukemia virus, which vaccine comprises:
   (a) an immunologically effective amount of an FeLV antigen;
   (b) an immunopotentiating amount of an immunostimulating glycopeptide, wherein said glycopeptide is a compound of the formula

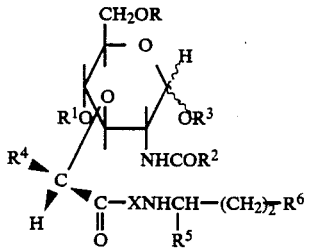

(I)

wherein

R and $R^1$ are the same or different and are hydrogen or acyl containing from 1 to 22 carbon atoms;

$R^2$ is an unsubstituted or substituted alkyl radical containing from 1 to 22 carbon atoms, or an unsubstituted or substituted aryl radical containing from 6 to 10 carbon atoms;

$R^3$ is hydrogen, alkyl, or aryl of 7 to 10 carbon atoms;

$R^4$ is hydrogen or alkyl;

X is alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl, $R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;

(c) a multi-phase-forming amount between 0.2 and 49% v/v of the vaccine of a non-toxic polyoxypropylene-polyoxyethylene block polymer, wherein said block polymer is liquid over a temperature range between about 15°–40° C., has a polyoxypropylene midsection of molecular weight between about 2250 and 4300, and has polyoxyethylene in an amount between about 1 and 30% of the block polymer;

(d) a multi-phase-stabilizing amount between 0.05 and 2.5% v/v of the vaccine of a glycol ether-based surfactant; and (e) buffered saline in a quantity sufficient to make volume.

2. The vaccine of claim 1 having the glycopeptide of Formula (I) wherein

R and $R^1$ are the same or different and are hydrogen or an acyl radical containing from 1 to 22 carbon atoms;

$R^2$ is methyl;

$R^3$ is hydrogen; and

X is L-seryl, L-alanyl, L-valyl, L-leucyl, L-isoleucyl, L-α-aminobutyryl, L-threonyl, L-methionyl, L-cysteinyl, L-phenylalanyl, L-tyrosyl, L-tryptophenyl, L-lysyl, L-ornithyl, L-arginyl, L-histidyl, L-glutamyl, L-glutamanyl, L-aspartyl, L-asparaginyl, L-prolyl, or L-hydroxyprolyl.

3. The vaccine of claim 2 wherein said glycopeptide is a compound of Formula (I) wherein R, $R^1$ and $R^3$ are hydrogen;

$R^2$ is methyl;

$R^4$ is methyl, butyl or hydrogen;

X is L-valyl, L-alanyl, L-seryl, L-threonyl or L-α-aminobutyryl;

$R^5$ is carboxyl, carbamoyl or n-butyl carboxylate; and $R^6$ is carboxyl or carbamoyl.

4. The vaccine of claim 3 wherein said glycopeptide is

N-acetylmuramyl-L-α-aminobutyryl-D-isoglutamine;

6-O-stearoyl-N-acetylmuramyl-L-α-aminobutyryl-D-isoglutamine;

N-acetylmuramyl-L-threonyl-D-isoglutamine;

N-acetylmuramyl-L-valyl-D-isoglutamine;

N-acetylmuramyl-L-alanyl-D-isoglutamine;

N-acetyl-desmethylmuramyl-L-alanyl-D-isoglutamine;

N-acetylmuramyl-L-alanyl-D-glutamine n-butyl ester;

N-acetylmuramyl-L-seryl-D-isoglutamine;

N-acetyl(butylmuramyl)-L-α-aminobutyryl-D-isoglutamine; or

N-acetyl(butylmuramyl)-L-alanyl-D-isoglutamine.

5. The vaccine of claim 3 wherein said glycopeptide is

N-acetylmuramyl-L-threonyl-D-isoglutamine;

6-O-stearoyl-N-acetylmuramyl-L-α-aminobutyryl-D-isoglutamine;

N-acetyl-desmethylmuramyl-L-alanyl-D-isoglutamine; or

N-acetyl(butylmuramyl)-L-α-aminobutyryl-D-isoglutamine.

6. The vaccine of claim 5 wherein said glycopeptide is N-acetylmuramyl-L-threonyl-D-isoglutamine.

7. The vaccine of claim 1 wherein the glycopeptide is present in a concentration range of 0.001–5% (w/v).

8. The vaccine of claim 1 wherein the FeLV antigen is inactivated FeLV virus.

9. The vaccine of claim 8 wherein said inactivated FeLV virus is derived from persistently viremic normal cat embryo cells designated as NCE-F161.

10. The vaccine of claim 1 wherein said block polymer has a polyoxypropylene midsection of molecular weight between 3,000 and 4,000 and the percent polyoxyethylene in the block polymer comprises 0.2 to 20% (w/v).

11. The vaccine of claim 10 wherein said block polymer has a polyoxypropylene midsection of molecular weight between 3,250 and 4,000 and wherein the percentage of polyoxyethylene in the block polymer is 1–30% (w/w).

12. The vaccine of claim 1 wherein said block polymer is comprised of a polyoxypropylene midsection of molecular weight 3,250 and has a percentage polyoxyethylene in the block polymer of 10%.

13. The vaccine of claim 12 wherein the block polymer is present in an amount of 0.2–49% (v/v).

14. The vaccine of claim 13 wherein the block polymer is present in an amount of 0.2–20% (v/v).

15. The vaccine of claim 14 wherein the block polymer is present in an amount of 1–5% (v/v).

16. The vaccine of claim 15 wherein the block polymer is present in an amount of 2.5% (v/v).

17. The vaccine of claim 1 wherein said surfactant is a sorbitan-based surfactant.

18. The vaccine of claim 17 wherein said surfactant is polyoxyethylene 20 sorbitan monooleate.

19. The vaccine of claim 1 wherein said surfactant is present in an amount of 0.2–1% (w/v).

20. The vaccine of claim 1 which further comprises a non-toxic metabolizable oil, present in an amount of 1–30% (w/v).

21. The vaccine of claim 25 which further comprises a non-toxic metabolizable oil, present in an amount of 1–30% (w/v).

22. A method for enhancing the immunogenicity of an FeLV antigen which method comprises combining an immunologically effective amount of an FeLV antigen with an adjuvant composition comprising:

an immunopotentiating amount of an immunostimulating glycopeptide, wherein said glycopeptide is a compound of the formula

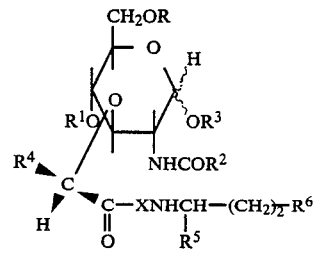

wherein

R and $R^1$ are the same or different and are hydrogen or acyl containing from 1 to 22 carbon atoms;

$R^2$ is an unsubstituted or substituted alkyl radical containing from 1 to 22 carbon atoms, or an unsubstituted or substituted aryl radical containing from 6 to 10 carbon atoms;

$R^3$ is hydrogen, alkyl, or aryl of 7 to 10 carbon atoms;

$R^4$ is hydrogen or alkyl;

X is alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxypropyl, seryl, or glycyl;

$R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;

a multi-phase-forming amount between 0.2 and 49% v/v of the vaccine of a non-toxic polyoxypropylene-polyoxyethylene block polymer, wherein said block polymer is liquid over a temperature range between about 15°–40° C., has a polyoxypropylene midsection of molecular weight between about 2250 and 4300, and has polyoxyethylene in an amount between about 1 and 30% of the block polymer;

a multi-phase-stabilizing amount between 0.05 and 2.5% v/v of the vaccine of a glycol ether-based surfactant; and buffered saline in a quantity sufficient to make volume.

23. A method for producing an immune response in a cat which method comprises administering to said cat an effective amount of a vaccine comprising:

(a) an immunologically effective amount of an FeLV antigen;

(b) an immunopotentiating amount of an immunostimulating glycopeptide, wherein said glycopeptide is a compound of the formula

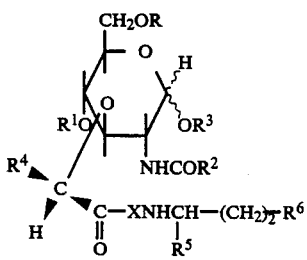

(I)

wherein

R and R¹ are the same or different and are hydrogen or acyl containing from 1 to 22 carbon atoms;

R² is an unsubstituted or substituted alkyl radical containing from 1 to 22 carbon atoms, or an unsubstituted or substituted aryl radical containing from 6 to 10 carbon atoms;

R³ is hydrogen, alkyl, or aryl of 7 to 10 carbon atoms;

R⁴ is hydrogen or alkyl;

X is alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl;

R⁵ and R⁶ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;

(c) a multi-phase-forming amount between 0.2 and 49% v/v of the vaccine of a non-toxic polyoxypropylene-polyoxyethylene block polymer, wherein said block polymer is liquid over a temperature range between about 15°–40° C., has a polyoxypropylene midsection of molecular weight between about 2250 and 4300, and has polyoxyethylene in an amount between about 1 and 30% of the block polymer;

(d) a multi-phase-stabilizing amount between 0.05 and 2.5% v/v of the vaccine of a glycol ether-based surfactant; and (e) buffered saline in a quantity sufficient to make volume.

24. A vaccine for immunizing a cat against feline leukemia virus, which vaccine comprises:
(a) an immunologically effective amount of an FeLV antigen derived from inactivated R-FeLV virus grown in NCE-F161 cells;
(b) 0.001 to 5% (w/v) N-acetylmuramyl-L-threonyl-D-isoglutamine;
(c) 2.5% (w/v) polyoxypropylene-polyoxyethylene block polymer having a polyoxypropylene midsection of molecular weight 3,250 wherein polyoxyethylene comprises 10% of the polymer;
(d) 0.2–1% (w/v) polyoxyethylene 20 sorbitan monooleate surfactant; and
(e) phosphate-buffered saline.

25. A vaccine for immunizing a cat against feline leukemia virus, which vaccine comprises:
a. an immunologically effective amount of a FeLV antigen derived from inactivated R-FeLV virus grown in NCE-F161 cells;
b. 0.001 to 5% (w/v) N-acetylmuramyl-L-threonyl-D-isoglutamine;
c. 2.5% (v/v) polyoxypropylene-polyoxyethylene block polymer having a polyoxypropylene midsection of molecular weight 3,250 and a polyoxyethylene component comprising 10% of the total polymer;
d. 0.2–1% (v/v) polyoxyethylene 20 sorbitan monooleate surfactant; and
e. phosphate-buffered saline.

26. A vaccine for immunizing a cat against feline leukemia virus, which vaccine comprises:
a. an immunologically effective amount of a FeLV antigen derived from inactivated R-FeLV virus grown in NCE-F161 cells;
b. 0.003% (w/v) N-acetylmuramyl-L-threonyl-D-isoglutamine;
c. 2.5% (v/v) polyoxypropylene-polyoxyethylene block polymer having a polyoxypropylene midsection of molecular weight 3,250 and a polyoxyethylene component comprising 10% of the total polymer;
d. 0.2–1% (v/v) polyoxyethylene 20 sorbitan monooleate surfactant; and
e. phosphate-buffered saline.

* * * * *